US012516305B2

(12) United States Patent
Li et al.

(10) Patent No.: US 12,516,305 B2
(45) Date of Patent: *Jan. 6, 2026

(54) BETA-GLYCOSIDASE SS-BGL MUTANT FOR MODIFYING GINSENOSIDE AND APPLICATION THEREOF

(71) Applicant: Northwest University, Xi'an (CN)

(72) Inventors: Weina Li, Xi'an (CN); Daidi Fan, Xi'an (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/676,494

(22) Filed: May 28, 2024

(65) Prior Publication Data

US 2024/0401093 A1 Dec. 5, 2024

(51) Int. Cl.

| | |
|---|---|
| ***C12N 9/42*** | (2006.01) |
| ***C12N 15/70*** | (2006.01) |
| ***C12P 15/00*** | (2006.01) |
| ***C12P 33/20*** | (2006.01) |

(52) U.S. Cl.

CPC ........... *C12N 9/2445* (2013.01); *C12N 15/70* (2013.01); *C12P 15/00* (2013.01); *C12P 33/20* (2013.01); *C12Y 302/01021* (2013.01)

(58) Field of Classification Search

CPC .... C12N 9/2445; C12N 15/70; C12N 9/2402; C12N 9/2405; C12N 9/2428; C12N 9/2471; C12P 15/00; C12P 33/20; C12Y 302/01021; C12Y 302/0102; C12Y 302/01023; Y02A 50/30; C12R 2001/19

See application file for complete search history.

(56) References Cited

U.S. PATENT DOCUMENTS 12,258,598 B2 * 3/2025 Li ........................ C12N 9/2445

OTHER PUBLICATIONS

Bismuto et al., Dynamic fluorescence studies of b-glycosidase mutants from Sulfolobus solfataricus: effects of single mutations on protein thermostability. Proteins: Structure, Function and Genetics, 2003, vol. 51:10-20. (Year: 2003).*

Broun et al., Catalytic plasticity of fatty acid modification enzymes underlying chemical diversity of plant lipids. Science, 1998, vol. 282: 1315-1317. (Year: 1998).*

Devos et al., Practical limits of function prediction. Proteins: Structure, Function, and Genetics. 2000, vol. 41: 98-107. (Year: 2000).*

Perugino et al., Effects of random mutagenesis and in vivo selection on the specificity and stability of a thermozyme. Catalysts, 2019, vol. 9, 440, pp. 1-15. (Year: 2019).*

Seffernick et al., Melamine deaminase and Atrazine chlorohydrolase: 98 percent identical but functionally different. J. Bacteriol., 2001, vol. 183 (8): 2405-2410. (Year: 2001).*

Shen et al., Residue effect-guided design: engineering of S. solfataricus b-glycosidase to enhance its thermostability and bioproduction of ginsenoside compound K. J. Agric. Food Chem., 2023, vol. 71: 16669-16680. (Year: 2023).*

Whisstock et al., Prediction of protein function from protein sequence. Q. Rev. Biophysics., 2003, vol. 36 (3): 307-340. (Year: 2003).*

Witkowski et al., Conversion of b-ketoacyl synthase to a Malonyl Decarboxylase by replacement of the active cysteine with glutamine. Biochemistry, 1999, vol. 38: 11643-11650. (Year: 1999).*

* cited by examiner

*Primary Examiner* — Ganapathirama Raghu

(74) *Attorney, Agent, or Firm* — Addison D. Ault; IPGentleman Intellectual Property Services, LLC

(57) ABSTRACT

A β-glycosidase SS-BGL mutant for modifying ginsenoside and an application thereof are provided, which relate to the field of genetic engineering technologies. The β-glycosidase SS-BGL mutant is a mutant mutating asparagines at 128$^{th}$ position and 302$^{th}$ position of the amino acid sequence as shown in SEQ ID NO: 1 of β-glycosidase SS-BGL into aspartic acids respectively. The β-glucosidase SS-BGL mutant improves the thermal stability of the natural β-glucosidase SS-BGL at extremely high temperature, and is more conducive to the application of SS-BGL in ginsenoside preparation.

7 Claims, 2 Drawing Sheets

Specification includes a Sequence Listing.

BETA-GLYCOSIDASE SS-BGL MUTANT FOR MODIFYING GINSENOSIDE AND APPLICATION THEREOF

CROSS-REFERENCE TO RELATED APPLICATION

This application claims priority to Chinese Patent Application No. 202311285240.6, filed May 30, 2023, which is herein incorporated by reference in its entirety.

TECHNICAL FIELD

The disclosure relates to the field of genetic engineering technologies, and more particularly to a beta-glycosidase (β-glycosidase) SS-BGL mutant for modifying ginsenoside and an application thereof.

STATEMENT REGARDING SEQUENCE LISTING

The sequence listing associated with this application is provided in text format in lieu of a paper copy and is hereby incorporated by reference into the specification. The name of the XML file containing the sequence listing is 24004MYZ-USP1-SL-R.xml. The XML file is 29,578 bytes; is created on Jun. 25, 2025; and is being submitted electronically via patent center. No new matter is entered.

BACKGROUND

In recent years, as one of main active ingredients of *Panax ginseng*, saponin components have attracted attention due to their extensive anti-cancer activity. Research found that a secondary metabolite "rare ginsenoside" of ginsenoside shows a stronger anti-cancer activity, which can be obtained through in vitro degradation of total saponins. A ginsenoside compound K (20-O-β-D-glucopyranosyl-20 (S)-protopanaxadiol, CK) is a main deglycosylated metabolite of the ginsenoside, which shows various interesting biological activities such as anti-cancer, anti-diabetic, anti-inflammatory, anti-allergic, anti-angiogenic, anti-aging, neuroprotective, and hepatoprotective effects. However, a preparation of the CK is difficult, which greatly suppresses a further application of the CK. In order to improve a production of the CK, multiple methods are developed to prepare the CK at present.

A structural modification of the ginsenoside mainly involves in hydrolysis of glycosyl at a specific site. Glycosidase is one of the most common industrial enzymes, which is responsible for hydrolysis and cleavage of glycosidic bonds, and is used as a catalyst for lactose hydrolysis in dairy products in a food industry. Due to extensive hydrolytic activities such as β-D-glucosidase, β-D-galactosidase, β-D-hydroxy glucosidase and α-glucosidase activities, β-glycosidase (SS-BGL with the amino acid sequence as shown in SEQ ID NO: 1) from thermophilic archaea *Sulfolobus solfataricus* (a growth environment temperature is 87 Celsius degrees abbreviated as ° C., and a power of hydrogen abbreviated as pH is 3.0) has been confirmed to be an efficient CK producing enzyme using glycosylated protopanaxadiol (PPD) type ginsenosides as substrates. A hydrolysis pathway of SS-BGL preparing the rare ginsenoside CK with ginsenoside Rb1 as a substrate is as follows: Rb1→Rd→F2→CK. A high temperature means a high reaction rate and lower pollution, and thermophilic glycosidase have excellent advantages in industrial applications. Research shows that stability of the SS-BGL (an optimal temperature is 85° C. and an optimal pH is 5.5) will rapidly decrease above its optimal temperature, which greatly limits a further application of the SS-BGL.

SUMMARY

In order to solve the above technical problems, the disclosure provides a β-glycosidase SS-BGL mutant with improved thermal stability and an application thereof.

According to a first aspect, the disclosure provides a β-glycosidase SS-BGL mutant for modifying ginsenoside, and the β-glycosidase SS-BGL mutant is a mutant mutating asparagines at 128$^{th}$ position and 302$^{th}$ position of the amino acid sequence as shown in SEQ ID NO: 1 of β-glycosidase SS-BGL into aspartic acids respectively.

According to a second aspect, the disclosure provides an application method of the β-glycosidase SS-BGL mutant, and the application method includes: preparing the ginsenoside by using the β-glycosidase SS-BGL mutant.

According to a third aspect, the disclosure provides a gene encoding the β-glycosidase SS-BGL mutant.

According to a fourth aspect, the disclosure provides a recombinant expression vector carrying the gene.

In an embodiment, the recombinant expression vector uses a pET-24a(+) vector as an original expression vector.

According to a fifth aspect, the disclosure provides a genetically engineered bacterium converted by the recombinant expression vector.

In an embodiment, the genetically engineered bacterium takes *Escherichia coli* BL21 (DE3) as a host.

The disclosure has the following beneficial effects.

(1) On the basis of natural β-glycosidase SS-BGL (i.e., wild type β-glycosidase SS-BGL), the molecular structure of the β-glycosidase SS-BGL is modified by rational design and site-directed mutation biotechnology, and the influence of mutated residues on the thermal stability of the enzyme is analyzed, and finally combined mutant strains (mutant strains Q96E/N97D/N302D and Q96E/N97D/N128D/N302D) with improved stability and saponin conversion activity are obtained.

(2) The melting temperature $T_m$ of the natural β-glycosidase SS-BGL is 89.62° C., and the melting temperature $T_m$ of the β-glycosidase SS-BGL mutant Q96E/N97D/N302D provided by the disclosure reaches 102.23° C., which is 12.61° C. higher than that of the natural-glycosidase SS-BGL. The melting temperature $T_m$ of the β-glycosidase SS-BGL mutant Q96E/N97D/N128D/N302D reaches 103.89° C., which is 14.27° C. higher than that of the natural β-glycosidase SS-BGL.

(3) The thermal stability of the β-glycosidase SS-BGL mutant provided by the disclosure is significantly improved, while the saponin conversion activity of the β-glycosidase SS-BGL mutant is greatly improved. The relative enzyme activity of the β-glycosidase SS-BGL mutants Q96E/N97D/N302D and Q96E/N97D/N128D/N302D for saponin conversion at 95° C. are 160.83% and 115.95%, respectively.

The β-glycosidase SS-BGL mutants obtained by the disclosure improve the thermal stability of the natural β-glycosidase SS-BGL at extremely high temperature, and is more conducive to the application of the β-glycosidase SS-BGL in the preparation of the ginsenoside.

DETAILED DESCRIPTION OF EMBODIMENTS

Figure 1:
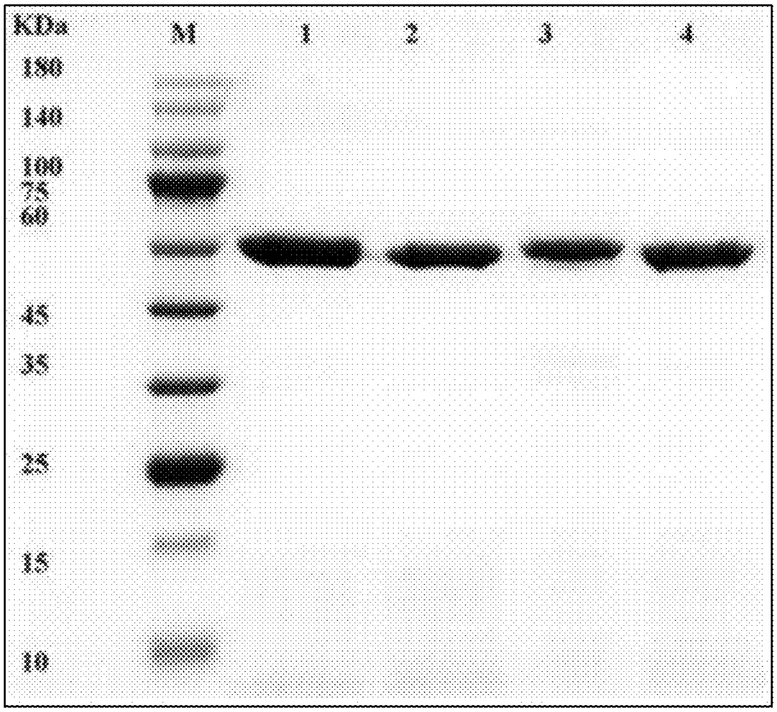
FIG. 1 illustrates a schematic diagram of bands of pure protein solutions of a wild type (WT) β-glycosidase SS- BGL, a β-glycosidase SS-BGL mutant N128D/N302D (with the amino acid sequence of SEQ ID NO: 18), a β-glycosidase SS-BGL mutant Q96E/N97D/N302D, and a β-glycosidase SS-BGL mutant Q96E/N97D/N128D/N302D after a sodium dodecyl sulfate polyacrylamide gel electrophoresis (SDA-PAGE) analysis according to an embodiment of the disclosure.

The disclosure will be described in detail in conjunction with drawings and embodiments below, but it should not be understood as a limitation of the disclosure. Unless otherwise specified, technical means used in the following embodiments are conventional means well known to those skilled in the art, and materials and reagents used in the following embodiments can be obtained from commercial sources unless otherwise specified.

In the following embodiments, the media and formulas involved are as follows:

Luria-Bertani (LB) liquid medium: 10 grams per liter (g/L) peptone, 5 g/L yeast powder, and 10 g/L sodium chloride (NaCl).

LB solid medium: 2% agar is added to the LB liquid medium.

The detection methods involved in the following embodiments are as follows.

A determination method of enzyme activity of β-glycosidase SS-BGL is as follows.

(1) The enzyme activity is determined by detecting a release amount of 4-nitrophenol in 4-nitrophenyl β-D-glucopyranoside (pNPG). 100 microliters (μL) of 1.0 milligram per milliliter (mg/mL) enzyme solution is added into 600 μL of 4 millimoles per liter (mM) pNPG solution to react at 85° C. for 10 minutes (min) to obtain a reacted solution, and 200 μL of 1 mM sodium carbonate solution is added into the reacted solution to terminate the reaction. The release amount of the 4-nitrophenol is obtained by testing an absorbance at 405 nanometers (nm). The enzyme activity is defined as an amount of enzyme required to release 1 micromole (μmol) of the 4-nitrophenol per min. All experiments are conducted three parallel experiments.

(2) 5 mg/mL ginsenoside Rb1 is used as a substrate, 1 milliliter (mL) of 1.0 mg/mL enzyme solution dissolved in 50 mM citric acid/phosphate buffer solution is added into the substrate to react at 95° C. for 1 hour (h) to obtain a reacted solution, and equal volume methanol is added into the reacted solution to terminate the reaction to obtain a mixed solution. An ultrasonic treatment is performed on the mixed solution for 30 min, and the mixed solution after the ultrasonic treatment is filtered with 0.45 microns (μm) sterile filter head. Generation of CK is detected by a high-performance liquid chromatography (HPLC). The enzyme activity is defined as an amount of enzyme required to convert 1 μmol of the ginsenoside Rb1 per min at 95° C. and pH 5.5, which is an enzyme activity unit abbreviated as U.

Embodiment 1: Construction of Recombinant Plasmids of β-Glycosidase SS-BGL Mutants (1) Construction of Recombinant Plasmids Containing Wild Type β-Glycosidase SS-BGL The gene sequence of the wild type β-glucosidase SS-BGL shown in SEQ ID NO: 2 is chemically synthesized, and the gene sequence of the wild type β-glucosidase SS-BGL and a pET-24a(+) are ligated after digesting by using BamH I enzyme and EcoR I enzyme to obtain a recombinant vector pET-24a(+)-SS-BGL.

(2) Acquisition of Recombinant Plasmids Containing the β-Glycosidase SS-BGL Mutants The recombinant vector pET-24a(+)-SS-BGL prepared in the step (1) is used as a template for site-directed mutation by using a whole plasmid polymerase chain reaction (PCR) technique, to obtain recombinant plasmids containing mutant gene:

pET-24a(+)-SS-BGL-Q96E (Q96E: making glutamine at 96$^{th}$ position of the amino acid sequence as shown in SEQ ID NO: 1 to be mutated to glutamic acid);

pET-24a(+)-SS-BGL-N97D (N97D: making asparagine at 97$^{th}$ position of the amino acid sequence as shown in SEQ ID NO: 1 to be mutated to aspartic acid);

pET-24a(+)-SS-BGL-N128D (N128D: making asparagine at 128$^{th}$ position of the amino acid sequence as shown in SEQ ID NO: 1 to be mutated to aspartic acid);

pET-24a(+)-SS-BGL-N302D (N302D: making asparagine at 302$^{th}$ position of the amino acid sequence as shown in SEQ ID NO: 1 to be mutated to aspartic acid);

pET-24a(+)-SS-BGL-N128D/N302D (N128D/N302D: a combination of N128D and N302D);

pET-24a(+)-SS-BGL-Q96E/N97D/N302D (Q96E/N97D/N302D: a combination of Q96E, N97D, and N302D); and pET-24a(+)-SS-BGL-Q96E/N97D/N128D/N302D (Q96E/N97D/N128D/N302D: a combination of Q96E, N97D, N128D, and N302D).

Primer sequences are designed as follows:

```
Q96E_F (as shown in SEQ ID NO: 3):
GCGCCCGGAGAATTTTGATGAAAGCAAACAGGATG;

Q96E_R (as shown in SEQ ID NO: 4):
TCAAAATTCTCCGGGCGCGGCAGCGGATTCGGAAA;

N97D_F (as shown in SEQ ID NO: 5):
GCGCCCGCAGGATTTTGATGAAAGCAAACAGGATG;

N97D_R (as shown in SEQ ID NO: 6):
TCAAAATCCTCCGGGCGCGGCAGCGGATTCGGAAA;

N128D_F (as shown in SEQ ID NO: 7):
TGCACTGGACCATTATCGTGAAATCTTTAAAGATC;

N128D_R (as shown in SEQ ID NO: 8):
CGATAATGGTCCAGTGCATCTTTATTTGCATATTC;

N302D_F (as shown in SEQ ID NO: 9):
CCCGTGGTGATGAAAAAATTGTTCGTGATGATCTG;
and
```

-continued

```
N302D_R (as shown in SEQ ID NO: 10):
TTTTTTCATCACCACGGGTAATTTCACCACGAATG.
```

Specifically, the PCR amplification program is set as follows: firstly, pre-denaturation at 95° C. for 30 seconds(s); then 30 cycles; denaturation at 95° C. for 15 s, annealing at 60° C. for 15 s, extension at 72° C. for 7 min, and heat preservation at 4° C. PCR products are detected by 1.0% agarose gel electrophoresis.

The final amplification fragment is treated with Dpn I enzyme at 37° C. for 1 h to remove the template, then a recombinant reaction is performed on the final amplification fragment without template at 50° C. for 20 min by using 2×Hieff clone enzyme premix to obtain a recombinant mixture. The recombinant mixture is transformed into *Escherichia coli* (*E. coli*) DH5a competent cells, to obtain a transformed solution. The transformed solution is coated on an LB solid medium containing kanamycin (50 micrograms per milliliter abbreviated as μg/mL), and the plasmid is extracted and sequenced. The sequencing work is completed by Sangon Biotech (Shanghai) Co., Ltd.

Embodiment 2: Expression, Separation and Purification of the β-Glycosidase SS-BGL Mutants (1) Construction of Genetically Engineered Bacteria Containing the Recombinant Plasmids The recombinant plasmids obtained in the embodiment 1 are transformed onto the *E. coli* BL21 (DE3) competent cells, to respectively obtain the following genetically engineered bacteria:

*E. coli*/pET-24a(+)-SS-BGL-Q96E;
*E. coli*/pET-24a(+)-SS-BGL-N97D;
*E. coli*/pET-24a(+)-SS-BGL-N128D;
*E. coli*/pET-24a(+)-SS-BGL-N302D;
*E. coli*/pET-24a(+)-SS-BGL-N128D/N302D;
*E. coli*/pET-24a(+)-SS-BGL-Q96E/N128D/N302D; and
*E. coli*/pET-24a(+)-SS-BGL-Q96E/N97D/N128D/N302D.

(2) Induced Expression of the β-Glycosidase SS-BGL Mutants

The genetically engineered bacteria prepared in the step (1) are inoculated into 10 mL of the LB liquid medium containing 50 μg/mL kanamycin, and cultured overnight at 37° C. and 220 revolutions per minute (rpm) to prepare seed solutions respectively. The prepared seed solutions each are transferred to 100 mL of the LB liquid medium containing 50 μg/mL kanamycin according to the inoculation amount of 0.5% (v/v), cultured at 37° C. and 220 rpm until an optical density at a wavelength 600 nm (OD600) is 0.6, added isopropylthio-β-galactoside (IPTG) with a final concentration of 1 mM, and continue to culture at 16° C. for 16 h to obtain fermentation solutions. The prepared fermentation solutions each are centrifuged at 10000 rpm and 4° C. for 5 min to obtain cell thalli, and the cell thalli are re-suspended with 50 mM citric acid/phosphate buffer solution. The re-suspended cell thalli are treated with an ultrasonic crusher in an ice bath for 10 min, centrifuged for 10 min (10000 rpm, 4° C.), and supernatants are taken to obtain crude enzyme solutions.

(3) Separation and Purification of the β-Glycosidase SS-BGL Mutants

The crude enzyme solutions each are heated at 80° C. for 30 min, and filtered with 0.45 μm sterile filter membrane to obtain filtrates. The filtrates are pure enzyme solutions, and protein concentrations of the pure enzyme solutions are detected by using a bicin-choninic acid (BCA) protein colorimetric assay kit.

The obtained pure enzyme solutions are individually analyzed by the SDS-PAGE to obtain results shown in FIG. 1. The results show that there is an obvious band at 60 kilodaltons (kDa), which proves that the β-glycosidase SS-BGL is expressed.

(4) Thermal Stability Research of the β-Glycosidase SS-BGL Mutants

The obtained pure enzyme solutions each are incubated in a constant temperature vacuum drying oven at 95° C. for 30 min, and then taken out to detect residual enzyme activity. Percentages of the residual enzyme activity are obtained by taking the enzyme activity of the pure enzyme solution without high-temperature treatment as a blank control. The test results are shown in Table 1.

TABLE 1

Residual enzyme activity after heat treatment at 95° C. for 30 min

| Enzyme | Residual enzyme activity (%) |
|---|---|
| WT | 98.45 |
| Q96E | 99.00 |
| N97D | 98.71 |
| N128D | 99.23 |
| N302D | 98.70 |

It can be seen from Table 1 that the single-site mutants each retain higher enzyme activity than the wild type enzyme, and the double-site mutant N128D/N302D, the three-site mutant Q96E/N97D/N302D and the four-site mutant Q96E/N97D/N128D/N302D are obtained by superimposing the above single-site mutations. The steps (2) and (3) are repeated to obtain pure enzyme solutions of the above multi-mutants, and the pure enzyme solutions of the above multi-mutants are placed at 95° C. for 2 h, and residual enzyme activity of each multi-mutant is tested. Results are shown in Table 2.

TABLE 2

Residual enzyme activity of multi-mutants after heat treatment at 95° C. for 2 h

| Enzyme | Residual enzyme activity (%) |
|---|---|
| WT | 32.93 |
| N128D/N302D | 8.86 |
| Q96E/N97D/N302D | 84.60 |
| Q96E/N97D/N128D/N302D | 93.10 |

It can be seen from Table 2 that after incubation at 95° C. for 2 h, except for the residual enzyme activity of the double-site mutant N128D/N302D is lower than that of the wild type enzyme, the three-site mutant Q96E/N97D/N302D and the four-site mutant Q96E/N97D/N128D/N302D retain higher residual enzyme activity after heat treatment.

(5) Test of Effect of the Mutations on the Enzyme Activity

Initial relative enzyme activity determination is performed on the pure enzyme solutions prepared in the step (3) by using pNPG as a substrate, and the pure enzyme solutions containing the wild type β-glycosidase SS-BGL, the β-glycosidase SS-BGL mutant Q96E (as shown in SEQ ID NO: 11), the β-glycosidase SS-BGL mutant N97D (as shown in SEQ ID NO: 12), the β-glycosidase SS-BGL mutant N128D (as shown in SEQ ID NO: 13), the β-glycosidase SS-BGL mutant N302D (as shown in SEQ ID NO: 14), the β-glycosidase SS-BGL mutant N128D/N302D (as shown in SEQ ID NO: 15), the β-glycosidase SS-BGL mutant Q96E/N97D/302D (as shown in SEQ ID NO: 16) and the β-glycosidase SS-BGL mutant Q96E/N97D/N128D/N302D (as shown in SEQ ID NO: 17) prepared in the step (3) are tested, respectively. Results are shown in Table 3.

TABLE 3

Relative enzyme activity detected by using pNPG as substrate

| Enzyme | Relative enzyme activity (%) |
|---|---|
| WT | 100.00 |
| Q96E | 100.25 |
| N97D | 100.04 |
| N128D | 95.95 |
| N302D | 99.79 |
| N128D/N302D | 96.74 |
| Q96E/N97D/N302D | 99.74 |
| Q96E/N97D/N128D/N302D | 100.52 |

Figure 2:
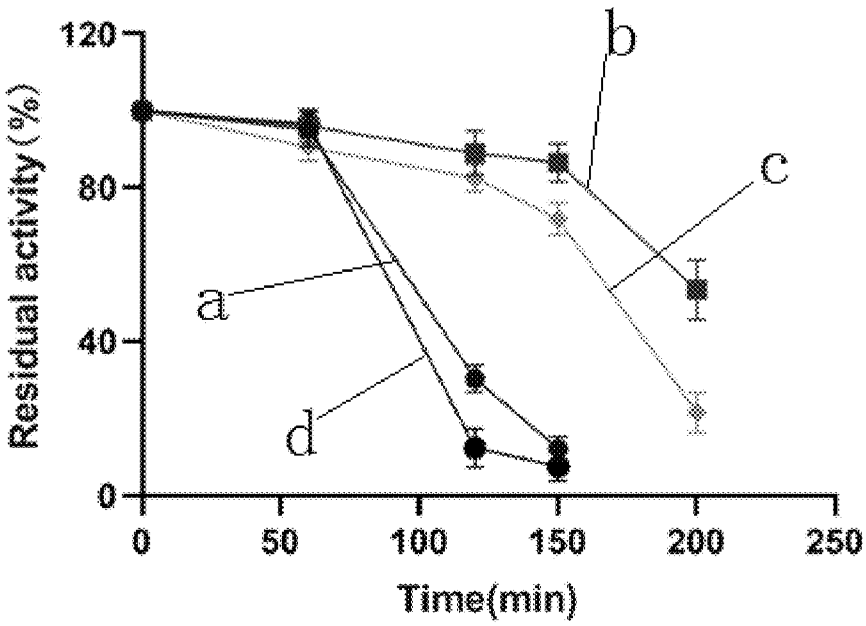
FIG. 2 illustrates a schematic diagram of test results of enzyme activity changes of the WT β-glycosidase SS-BGL (a), the β-glycosidase SS-BGL mutant N128D/N302D (b), the β-glycosidase SS-BGL mutant Q96E/N97D/N302D (c), and the β-glycosidase SS-BGL mutant Q96E/N97D/N128D/N302D (d) incubated at 95° C. for different time according to an embodiment of the disclosure.

Embodiment 3: Test of Enzymatic Properties of the β-Glycosidase SS-BGL Combination Mutants 1. Thermal Stability The pure enzyme solution containing the wild type β-glycosidase SS-BGL, the pure enzyme solution containing the β-glycosidase SS-BGL mutant N128D/N302D, the pure enzyme solution containing the β-glycosidase SS-BGL mutant Q96E/N97D/N302D and the pure enzyme solution containing the β-glycosidase SS-BGL mutant Q96E/N97D/N128D/N302D prepared in the step (3) of the embodiment 2 are taken, respectively, then put in a constant temperature constant temperature vacuum oven at 95° C., and sampled at certain time intervals. The residual enzyme activity of the above β-glycosidase SS-BGL is measured by using the pNPG method, and their thermal stability are compared. The test results are shown in FIG. 2. The enzyme activity decreases continuously over time. Except for the β-glycosidase SS-BGL combination mutant N128D/N302D, which has lower thermal stability than the wild type β-glycosidase SS-BGL, the β-glycosidase SS-BGL combination mutants Q96E/N97D/N302D and Q96E/N97D/N128D/N302D have higher thermal stability than the wild type β-glycosidase SS-BGL, and their half-lives are 2.5 and 3.3 times longer than the wild type β-glycosidase SS-BGL, respectively.

2. Optimum Temperature

Figure 3:
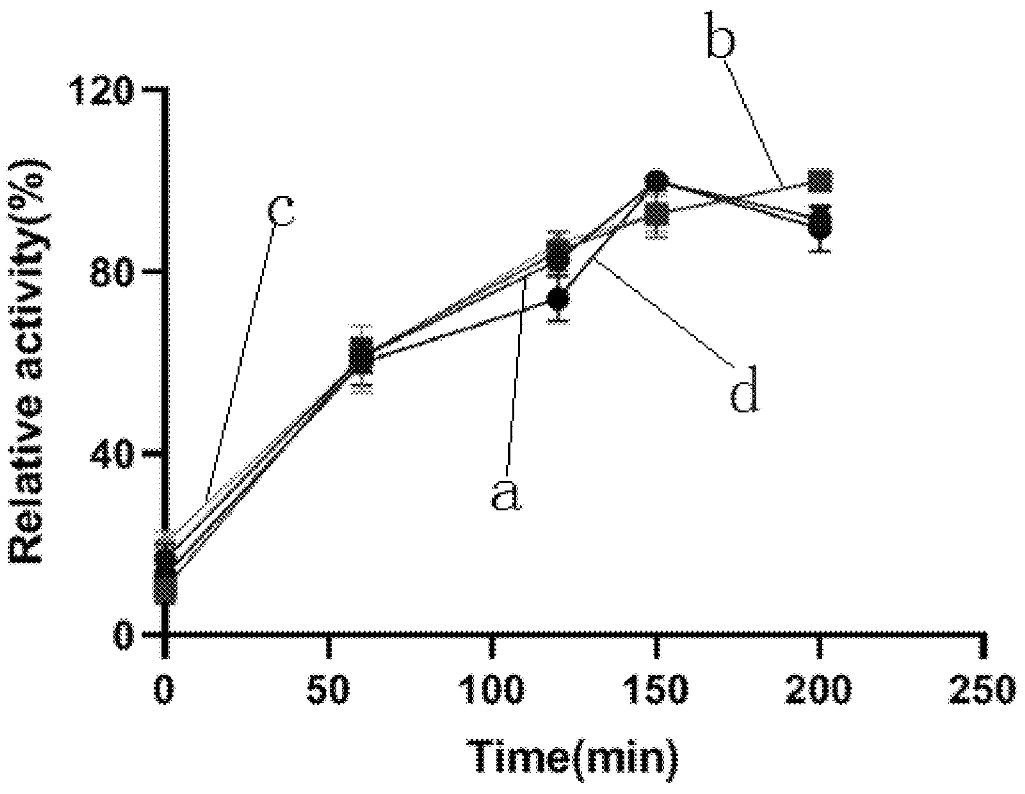
FIG. 3 illustrates a schematic diagram of test results of enzyme activity changes of the WT β-glycosidase SS-BGL (a), the β-glycosidase SS-BGL mutant N128D/N302D (b), the β-glycosidase SS-BGL mutant Q96E/N97D/N302D (c), and the β-glycosidase SS-BGL mutant Q96E/N97D/N128D/N302D (d) incubated at different temperatures according to an embodiment of the disclosure.

The enzyme activity is tested within a temperature range of 25° C. to 95° C., and test results are shown in FIG. 3. An optimum temperature of the β-glycosidase SS-BGL mutant N128D/N302D is 85° C., which is consistent with that of the wild type β-glycosidase SS-BGL. The β-glycosidase SS-BGL mutants Q96E/N97D/N302D and Q96E/N97D/N128D/N302D show higher enzyme activity at 95° C.

3. Kinetic Parameter

100 μL of each pure enzyme solution with a concentration of 1.0 mg/mL is taken, and respectively added with 2, 4, 6, 8, 10, 12, 14, 16 and 18 mM pNPG solutions to react at the optimum temperatures for 10 min, and then added with equal volume sodium carbonate to terminate the reaction to obtain a mixed solution. An absorbance detection is performed on the mixed solution. The test results are shown in Table 4.

TABLE 4

Kinetic parameter table

| Enzyme | $V_{max}$ (μM · min$^{-1}$) | $K_m$ (μM) | $K_{cat}$ (s$^{-1}$) | $K_{cat}/K_m$ (μM$^{-1}$ · s$^{-1}$) |
|---|---|---|---|---|
| WT | 82.23 ± 2.45 | 497.00 ± 178.70 | 351.41 ± 10.88 | 0.71 |
| N128D/N302D | 82.43 ± 2.74 | 556.31 ± 204.44 | 416.31 ± 13.84 | 0.75 |
| Q96E/N97D/N302D | 82.33 ± 2.39 | 487.50 ± 173.70 | 364.29 ± 10.58 | 0.75 |
| Q96E/N97D/N128D/N302D | 81.84 ± 2.06 | 441.94 ± 148.33 | 378.89 ± 9.54 | 0.86 |

4. Saponin Conversion 1 mL of each pure enzyme solution with the concentration of 1.0 mg/mL is taken, and added with 5.0 mg/mL ginsenoside Rb1 to react at 95° C. for 1 h, and then added with equal volume methanol to terminate the reaction to obtain a mixed solution. An ultrasonic treatment is performed on the mixed solution for 30 min, and the mixed solution after the ultrasonic treatment is filtered with 0.45 μL filter membrane, and generation of CK is detected by using the HPLC. Results are shown in Table 5.

TABLE 5

Relative enzyme activity after saponin conversion

| Enzyme | Relative enzyme activity (%) |
|---|---|
| WT | 100.00 |
| N128D/N302D | 179.37 |
| Q96E/N97D/N302D | 160.83 |
| Q96E/N97D/N128D/N302D | 115.95 |

Although the illustrated embodiments of the disclosure have been described, those skilled in the art may make additional changes and modifications to these embodiments once they have knowledge of the basic creative concepts. Therefore, attached claims are intended to be interpreted as including the embodiments and all changes and modifications falling within a scope of the disclosure.

Apparently, those skilled in the art can make various modifications and variations to the disclosure without departing from the spirit and scope of the disclosure. Thus, it is intended that the disclosure include these modifications and variations provided that they are within the scope of the claims and their equivalents.

SEQUENCE LISTING

```
Sequence total quantity: 18
SEQ ID NO: 1            moltype = AA  length = 489
FEATURE                 Location/Qualifiers
source                  1..489
                        mol_type = protein
                        organism = synthetic construct
SEQUENCE: 1
MYSFPNSFRF GWSQAGFQSE MGTPGSEDPN TDWYKWVHDP ENMAAGLVSG DLPENGPGYW  60
GNYKTFHDNA QKMGLKIARL NVEWSRIFPN PLPRPQNFDE SKQDVTEVEI NENELKRLDE  120
YANKDALNHY REIFKDLKSR GLYFILNMYH WPLPLWLHDP IRVRRGDFTG PSGWLSTRTV  180
YEFARFSAYI AWKFDDLVDE YSTMNEPNVV GGLGYVGVKS GFPPGYLSFE LSRRAMYNII  240
QAHARAYDGI KSVSKKPVGI IYANSSFQPL TDKDMEAVEM AENDNRWWFF DAIIRGEITR  300
GNEKIVRDDL KGRLDWIGVN YYTRTVVKRT EKGYVSLGGY GHGCERNSVS LAGLPTSDFG  360
WEFFPEGLYD VLTKYWNRYH LYMYVTENGI ADDADYQRPY YLVSHVYQVH RAINSGADVR  420
GYLHWSLADN YEWASGFSMR FGLLKVDYNT KRLYWRPSAL VYREIATNGA ITDEIEHLNS  480
VPPVKPLRH                                                          489

SEQ ID NO: 2            moltype = DNA  length = 1470
FEATURE                 Location/Qualifiers
source                  1..1470
                        mol_type = other DNA
                        organism = synthetic construct
SEQUENCE: 2
atgtatagct ttccgaatag ctttcgcttt ggttggtccc aggcaggttt tcagagcgaa  60
atgggtaccc cgggtagcga agatccgaac accgattggt ataaatgggt gcatgatccg  120
gaaaatatgg cagcaggtct ggttagcggt gatctgccag aaaatggtcc gggttattgg  180
ggtaactata aaacatttca tgataacgca cagaaaatgg gtctgaaaat tgcacgtctg  240
aacgttgaat ggagtcgtat ttttccgaat ccgctgccgc gcccgcagaa ttttgatgaa  300
agcaaacagg atgttaccga agtggaaatt aacgaaaatg aactgaaacg tctggatgaa  360
tatgcaaata aagatgcact gaaccattat cgtgaaatct ttaaagatct gaaaagccgt  420
ggcctgtatt ttatcctgaa tatgtatcat tggccgctgc cgctgtggct gcatgatcct  480
attcgcgttc gtcgtggtga ttttaccggt ccgtctggtt ggctgagcac ccgtactgtt  540
tatgaatttg cacgttttag cgcttatatt gcttggaaat ttgatgatct ggttgatgaa  600
tatagcacta tgaatgaacc gaacgttgtt ggtggtctgg gttatgttgg tgttaaaagc  660
ggttttccgc ctggttatct gagctttgaa ctgtcccgcc gtgcaatgta taatattatt  720
caggcacatg cgcgtgccta tgatggtatt aaaagcgttt ctaaaaagcc ggttggcatt  780
atttatgcga atagcagctt tcagcctctg accgataaag atatggaagc agttgaaatg  840
gcagaaaatg ataatcgttg gtggtttttt gatgcgatca ttcgtggtga aattacccgt  900
ggtaatgaaa aaattgttcg tgatgatctg aaaggtcgtc tggattggat tggtgttaat  960
tattataccc gtaccgttgt taaacgtacc gaaaaaggtt atgttagcct gggtggttat  1020
ggtcatggtt gtgaacgtaa tagcgttagc ctggcaggtc tgccgaccag cgattttggt  1080
tgggaatttt ttccggaagg tctgtatgat gttctgacca aatattggaa tcgttatcat  1140
ctgtatatgt atgttaccga aaatggtatt gcagatgatg cagattatca gcgtccgtat  1200
tatctggtta gccatgttta tcaggttcat cgtgcaatta atagcggtgc agatgttcgt  1260
ggttatctgc attggagcct ggcagataat tatgaatggg caagcggttt tagcatgcgt  1320
tttggtctgc tgaaagttga ttataatacc aaacgtctgt attggcgtcc gagcgcactg  1380
gtttatcgtg aaattgcaac caatggtgca attaccgatg aaattgaaca tctgaatagc  1440
gttccgccgg ttaaaccgct gcgtcattaa                                   1470

SEQ ID NO: 3            moltype = DNA  length = 35
FEATURE                 Location/Qualifiers
source                  1..35
                        mol_type = other DNA
                        organism = synthetic construct
SEQUENCE: 3
gcgcccggag aattttgatg aaagcaaaca ggatg                             35

SEQ ID NO: 4            moltype = DNA  length = 35
FEATURE                 Location/Qualifiers
source                  1..35
                        mol_type = other DNA
                        organism = synthetic construct
SEQUENCE: 4
tcaaaattct ccgggcgcgg cagcggattc ggaaa                             35

SEQ ID NO: 5            moltype = DNA  length = 35
FEATURE                 Location/Qualifiers
source                  1..35
                        mol_type = other DNA
                        organism = synthetic construct
SEQUENCE: 5
gcgcccgcag gattttgatg aaagcaaaca ggatg                             35

SEQ ID NO: 6            moltype = DNA  length = 35
FEATURE                 Location/Qualifiers
source                  1..35
                        mol_type = other DNA
                        organism = synthetic construct
```

-continued

```
SEQUENCE: 6
tcaaaatcct ccgggcgcgg cagcggattc ggaaa                          35

SEQ ID NO: 7           moltype = DNA  length = 35
FEATURE                Location/Qualifiers
source                 1..35
                       mol_type = other DNA
                       organism = synthetic construct
SEQUENCE: 7
tgcactggac cattatcgtg aaatctttaa agatc                          35

SEQ ID NO: 8           moltype = DNA  length = 35
FEATURE                Location/Qualifiers
source                 1..35
                       mol_type = other DNA
                       organism = synthetic construct
SEQUENCE: 8
cgataatggt ccagtgcatc tttatttgca tattc                          35

SEQ ID NO: 9           moltype = DNA  length = 35
FEATURE                Location/Qualifiers
source                 1..35
                       mol_type = other DNA
                       organism = synthetic construct
SEQUENCE: 9
cccgtggtga tgaaaaaatt gttcgtgatg atctg                          35

SEQ ID NO: 10          moltype = DNA  length = 35
FEATURE                Location/Qualifiers
source                 1..35
                       mol_type = other DNA
                       organism = synthetic construct
SEQUENCE: 10
ttttttcatc accacgggta atttcaccac gaatg                          35

SEQ ID NO: 11          moltype = DNA  length = 1470
FEATURE                Location/Qualifiers
source                 1..1470
                       mol_type = other DNA
                       organism = synthetic construct
SEQUENCE: 11
atgtatagct ttccgaatag ctttcgcttt ggttggtccc aggcaggttt tcagagcgaa  60
atgggtaccc cgggtagcga agatccgaac accgattggt ataaatgggt gcatgatccg  120
gaaaatatgg cagcaggtct ggttagcggt gatctgccag aaaatggtcc gggttattgg  180
ggtaactata aaacatttca tgataacgca cagaaaatgg gtctgaaaat tgcacgtctg  240
aacgttgaat ggagtcgtat ttttccgaat ccgctgccgc gcccggagaa ttttgatgaa  300
agcaaacagg atgttaccga agtggaaatt aacgaaaatg aactgaaacg tctggatgaa  360
tatgcaaata aagatgcact gaaccattat cgtgaaatct ttaaagatct gaaaagccgt  420
ggcctgtatt ttatcctgaa tatgtatcat tggccgctgc cgctgtggct gcatgatcct  480
attcgcgttc gtcgtggtga ttttaccggt ccgtctggtt ggctgagcac ccgtactgtt  540
tatgaatttg cacgttttag cgcttatatt gcttggaaat ttgatgatct ggttgatgaa  600
tatagcacta tgaatgaacc gaacgttgtt ggtggtctgg gttatgttgg tgttaaaagc  660
ggttttccgc ctggttatct gagctttgaa ctgtcccgcc gtgcaatgta taatattatt  720
caggcacatg cgcgtgccta tgatggtatt aaaagcgttt ctaaaaagcc ggttggcatt  780
atttatgcga atagcagctt tcagcctctg accgataaag atatggaagc agttgaaatg  840
gcagaaaatg ataatcgttg gtggtttttt gatgcgatca ttcgtggtga aattacccgt  900
ggtaatgaaa aaattgttcg tgatgatctg aaaggtcgtc tggattggat tggtgttaat  960
tattataccc gtaccgttgt taaacgtacc gaaaaaggtt atgttagcct gggtggttat  1020
ggtcatggtt gtgaacgtaa tagcgttagc ctggcaggtc tgccgaccag cgattttggt  1080
tgggaatttt ttccggaagg tctgtatgat gttctgacca aatattggaa tcgttatcat  1140
ctgtatatgt atgttaccga aaatggtatt gcagatgatg cagattatca gcgtccgtat  1200
tatctggtta gccatgttta tcaggttcat cgtgcaatta atagcggtgc agatgttcgt  1260
ggttatctgc attggagcct ggcagataat tatgaatggg caagcggttt tagcatgcgt  1320
tttggtctgc tgaaagttga ttataatacc aaacgtctgt attggcgtcc gagcgcactg  1380
gtttatcgtg aaattgcaac caatggtgca attaccgatg aaattgaaca tctgaatagc  1440
gttccgccgg ttaaaccgct gcgtcattaa                                1470

SEQ ID NO: 12          moltype = DNA  length = 1470
FEATURE                Location/Qualifiers
source                 1..1470
                       mol_type = other DNA
                       organism = synthetic construct
SEQUENCE: 12
atgtatagct ttccgaatag ctttcgcttt ggttggtccc aggcaggttt tcagagcgaa  60
atgggtaccc cgggtagcga agatccgaac accgattggt ataaatgggt gcatgatccg  120
gaaaatatgg cagcaggtct ggttagcggt gatctgccag aaaatggtcc gggttattgg  180
ggtaactata aaacatttca tgataacgca cagaaaatgg gtctgaaaat tgcacgtctg  240
aacgttgaat ggagtcgtat ttttccgaat ccgctgccgc gcccgcagga ttttgatgaa  300
agcaaacagg atgttaccga agtggaaatt aacgaaaatg aactgaaacg tctggatgaa  360
```

-continued tatgcaaata aagatgcact gaaccattat cgtgaaatct ttaaagatct gaaaagccgt 420
ggcctgtatt ttatcctgaa tatgtatcat tggccgctgc cgctgtggct gcatgatcct 480
attcgcgttc gtcgtggtga ttttaccggt ccgtctggtt ggctgagcac ccgtactgtt 540
tatgaatttg cacgttttag cgcttatatt gcttggaaat ttgatgatct ggttgatgaa 600
tatagcacta tgaatgaacc gaacgttgtt ggtggtctgg gttatgttgg tgttaaaagc 660
ggttttccgc ctggttatct gagctttgaa ctgtcccgcc gtgcaatgta taatattatt 720
caggcacatg cgcgtgccta tgatggtatt aaaagcgttt ctaaaaagcc ggttggcatt 780
atttatgcga atagcagctt tcagcctctg accgataaag atatggaagc agttgaaatg 840
gcagaaaatg ataatcgttg gtggtttttt gatgcgatca ttcgtggtga aattacccgt 900
ggtaatgaaa aaattgttcg tgatgatctg aaaggtcgtc tggattggat tggtgttaat 960
tattataccc gtaccgttgt taaacgtacc gaaaaaggtt atgttagcct gggtggttat 1020
ggtcatggtt gtgaacgtaa tagcgttagc ctggcaggtc tgccgaccag cgattttggt 1080
tgggaatttt ttccggaagg tctgtatgat gttctgacca aatattggaa tcgttatcat 1140
ctgtatatgt atgttaccga aaatggtatt gcagatgatg cagattatca gcgtccgtat 1200
tatctggtta gccatgttta tcaggttcat cgtgcaatta atagcggtgc agatgttcgt 1260
ggttatctgc attggagcct ggcagataat tatgaatggg caagcggttt tagcatgcgt 1320
tttggtctgc tgaaagttga ttataatacc aaacgtctgt attggcgtcc gagcgcactg 1380
gtttatcgtg aaattgcaac caatggtgca attaccgatg aaattgaaca tctgaatagc 1440
gttccgccgg ttaaaccgct gcgtcattaa 1470

SEQ ID NO: 13 moltype = DNA length = 1470
FEATURE Location/Qualifiers
source 1..1470
mol_type = other DNA
organism = synthetic construct
SEQUENCE: 13
atgtatagct ttccgaatag ctttcgcttt ggttggtccc aggcaggttt tcagagcgaa 60
atgggtaccc cgggtagcga agatccgaac accgattggt ataaatgggt gcatgatccg 120
gaaaatatgg cagcaggtct ggttagcggt gatctgccag aaaatggtcc gggttattgg 180
ggtaactata aaacatttca tgataacgca cagaaaatgg gtctgaaaat tgcacgtctg 240
aacgttgaat ggagtcgtat ttttccgaat ccgctgccgc gcccgcagaa ttttgatgaa 300
agcaaacagg atgttaccga agtggaaatt aacgaaaatg aactgaaacg tctggatgaa 360
tatgcaaata aagatgcact ggaccattat cgtgaaatct ttaaagatct gaaaagccgt 420
ggcctgtatt ttatcctgaa tatgtatcat tggccgctgc cgctgtggct gcatgatcct 480
attcgcgttc gtcgtggtga ttttaccggt ccgtctggtt ggctgagcac ccgtactgtt 540
tatgaatttg cacgttttag cgcttatatt gcttggaaat ttgatgatct ggttgatgaa 600
tatagcacta tgaatgaacc gaacgttgtt ggtggtctgg gttatgttgg tgttaaaagc 660
ggttttccgc ctggttatct gagctttgaa ctgtcccgcc gtgcaatgta taatattatt 720
caggcacatg cgcgtgccta tgatggtatt aaaagcgttt ctaaaaagcc ggttggcatt 780
atttatgcga atagcagctt tcagcctctg accgataaag atatggaagc agttgaaatg 840
gcagaaaatg ataatcgttg gtggtttttt gatgcgatca ttcgtggtga aattacccgt 900
ggtaatgaaa aaattgttcg tgatgatctg aaaggtcgtc tggattggat tggtgttaat 960
tattataccc gtaccgttgt taaacgtacc gaaaaaggtt atgttagcct gggtggttat 1020
ggtcatggtt gtgaacgtaa tagcgttagc ctggcaggtc tgccgaccag cgattttggt 1080
tgggaatttt ttccggaagg tctgtatgat gttctgacca aatattggaa tcgttatcat 1140
ctgtatatgt atgttaccga aaatggtatt gcagatgatg cagattatca gcgtccgtat 1200
tatctggtta gccatgttta tcaggttcat cgtgcaatta atagcggtgc agatgttcgt 1260
ggttatctgc attggagcct ggcagataat tatgaatggg caagcggttt tagcatgcgt 1320
tttggtctgc tgaaagttga ttataatacc aaacgtctgt attggcgtcc gagcgcactg 1380
gtttatcgtg aaattgcaac caatggtgca attaccgatg aaattgaaca tctgaatagc 1440
gttccgccgg ttaaaccgct gcgtcattaa 1470

SEQ ID NO: 14 moltype = DNA length = 1470
FEATURE Location/Qualifiers
source 1..1470
mol_type = other DNA
organism = synthetic construct
SEQUENCE: 14
atgtatagct ttccgaatag ctttcgcttt ggttggtccc aggcaggttt tcagagcgaa 60
atgggtaccc cgggtagcga agatccgaac accgattggt ataaatgggt gcatgatccg 120
gaaaatatgg cagcaggtct ggttagcggt gatctgccag aaaatggtcc gggttattgg 180
ggtaactata aaacatttca tgataacgca cagaaaatgg gtctgaaaat tgcacgtctg 240
aacgttgaat ggagtcgtat ttttccgaat ccgctgccgc gcccgcagaa ttttgatgaa 300
agcaaacagg atgttaccga agtggaaatt aacgaaaatg aactgaaacg tctggatgaa 360
tatgcaaata aagatgcact gaaccattat cgtgaaatct ttaaagatct gaaaagccgt 420
ggcctgtatt ttatcctgaa tatgtatcat tggccgctgc cgctgtggct gcatgatcct 480
attcgcgttc gtcgtggtga ttttaccggt ccgtctggtt ggctgagcac ccgtactgtt 540
tatgaatttg cacgttttag cgcttatatt gcttggaaat ttgatgatct ggttgatgaa 600
tatagcacta tgaatgaacc gaacgttgtt ggtggtctgg gttatgttgg tgttaaaagc 660
ggttttccgc ctggttatct gagctttgaa ctgtcccgcc gtgcaatgta taatattatt 720
caggcacatg cgcgtgccta tgatggtatt aaaagcgttt ctaaaaagcc ggttggcatt 780
atttatgcga atagcagctt tcagcctctg accgataaag atatggaagc agttgaaatg 840
gcagaaaatg ataatcgttg gtggtttttt gatgcgatca ttcgtggtga aattacccgt 900
ggtgatgaaa aaattgttcg tgatgatctg aaaggtcgtc tggattggat tggtgttaat 960
tattataccc gtaccgttgt taaacgtacc gaaaaaggtt atgttagcct gggtggttat 1020
ggtcatggtt gtgaacgtaa tagcgttagc ctggcaggtc tgccgaccag cgattttggt 1080
tgggaatttt ttccggaagg tctgtatgat gttctgacca aatattggaa tcgttatcat 1140
ctgtatatgt atgttaccga aaatggtatt gcagatgatg cagattatca gcgtccgtat 1200
tatctggtta gccatgttta tcaggttcat cgtgcaatta atagcggtgc agatgttcgt 1260

-continued

```
ggttatctgc attggagcct ggcagataat tatgaatggg caagcggttt tagcatgcgt  1320
tttggtctgc tgaaagttga ttataatacc aaacgtctgt attggcgtcc gagcgcactg  1380
gtttatcgtg aaattgcaac caatggtgca attaccgatg aaattgaaca tctgaatagc  1440
gttccgccgg ttaaaccgct gcgtcattaa                                    1470

SEQ ID NO: 15           moltype = DNA  length = 1470
FEATURE                 Location/Qualifiers
source                  1..1470
                        mol_type = other DNA
                        organism = synthetic construct
SEQUENCE: 15
atgtatagct ttccgaatag ctttcgcttt ggttggtccc aggcaggttt tcagagcgaa  60
atgggtaccc cgggtagcga agatccgaac accgattggt ataaatgggt gcatgatccg  120
gaaaatatgg cagcaggtct ggttagcggt gatctgccag aaaatggtcc gggttattgg  180
ggtaactata aaacatttca tgataacgca cagaaaatgg gtctgaaaat tgcacgtctg  240
aacgttgaat ggagtcgtat ttttccgaat ccgctgccgc gcccgcagaa ttttgatgaa  300
agcaaacagg atgttaccga agtggaaatt aacgaaaatg aactgaaacg tctggatgaa  360
tatgcaaata aagatgcact ggaccattat cgtgaaatct ttaaagatct gaaaagccgt  420
ggcctgtatt ttatcctgaa tatgtatcat tggccgctgc cgctgtggct gcatgatcct  480
attcgcgttc gtcgtggtga ttttaccggt ccgtctggtt ggctgagcac ccgtactgtt  540
tatgaatttg cacgttttag cgcttatatt gcttggaaat ttgatgatct ggttgatgaa  600
tatagcacta tgaatgaacc gaacgttgtt ggtggtctgg gttatgttgg tgttaaaagc  660
ggttttccgc ctggttatct gagctttgaa ctgtcccgcc gtgcaatgta taatattatt  720
caggcacatg cgcgtgccta tgatggtatt aaaagcgttt ctaaaaagcc ggttggcatt  780
atttatgcga atagcagctt tcagcctctg accgataaag atatggaagc agttgaaatg  840
gcagaaaatg ataatcgttg gtggtttttt gatgcgatca ttcgtggtga aattacccgt  900
ggtgatgaaa aaattgttcg tgatgatctg aaaggtcgtc tggattggat tggtgttaat  960
tattataccc gtaccgttgt taaacgtacc gaaaaaggtt atgttagcct gggtggttat  1020
ggtcatggtt gtgaacgtaa tagcgttagc ctggcaggtc tgccgaccag cgattttggt  1080
tgggaatttt ttccggaagg tctgtatgat gttctgacca aatattggaa tcgttatcat  1140
ctgtatatgt atgttaccga aaatggtatt gcagatgatg cagattatca gcgtccgtat  1200
tatctggtta gccatgttta tcaggttcat cgtgcaatta atagcggtgc agatgttcgt  1260
ggttatctgc attggagcct ggcagataat tatgaatggg caagcggttt tagcatgcgt  1320
tttggtctgc tgaaagttga ttataatacc aaacgtctgt attggcgtcc gagcgcactg  1380
gtttatcgtg aaattgcaac caatggtgca attaccgatg aaattgaaca tctgaatagc  1440
gttccgccgg ttaaaccgct gcgtcattaa                                    1470

SEQ ID NO: 16           moltype = DNA  length = 1470
FEATURE                 Location/Qualifiers
source                  1..1470
                        mol_type = other DNA
                        organism = synthetic construct
SEQUENCE: 16
atgtatagct ttccgaatag ctttcgcttt ggttggtccc aggcaggttt tcagagcgaa  60
atgggtaccc cgggtagcga agatccgaac accgattggt ataaatgggt gcatgatccg  120
gaaaatatgg cagcaggtct ggttagcggt gatctgccag aaaatggtcc gggttattgg  180
ggtaactata aaacatttca tgataacgca cagaaaatgg gtctgaaaat tgcacgtctg  240
aacgttgaat ggagtcgtat ttttccgaat ccgctgccgc gcccggagga ttttgatgaa  300
agcaaacagg atgttaccga agtggaaatt aacgaaaatg aactgaaacg tctggatgaa  360
tatgcaaata aagatgcact gaaccattat cgtgaaatct ttaaagatct gaaaagccgt  420
ggcctgtatt ttatcctgaa tatgtatcat tggccgctgc cgctgtggct gcatgatcct  480
attcgcgttc gtcgtggtga ttttaccggt ccgtctggtt ggctgagcac ccgtactgtt  540
tatgaatttg cacgttttag cgcttatatt gcttggaaat ttgatgatct ggttgatgaa  600
tatagcacta tgaatgaacc gaacgttgtt ggtggtctgg gttatgttgg tgttaaaagc  660
ggttttccgc ctggttatct gagctttgaa ctgtcccgcc gtgcaatgta taatattatt  720
caggcacatg cgcgtgccta tgatggtatt aaaagcgttt ctaaaaagcc ggttggcatt  780
atttatgcga atagcagctt tcagcctctg accgataaag atatggaagc agttgaaatg  840
gcagaaaatg ataatcgttg gtggtttttt gatgcgatca ttcgtggtga aattacccgt  900
ggtgatgaaa aaattgttcg tgatgatctg aaaggtcgtc tggattggat tggtgttaat  960
tattataccc gtaccgttgt taaacgtacc gaaaaaggtt atgttagcct gggtggttat  1020
ggtcatggtt gtgaacgtaa tagcgttagc ctggcaggtc tgccgaccag cgattttggt  1080
tgggaatttt ttccggaagg tctgtatgat gttctgacca aatattggaa tcgttatcat  1140
ctgtatatgt atgttaccga aaatggtatt gcagatgatg cagattatca gcgtccgtat  1200
tatctggtta gccatgttta tcaggttcat cgtgcaatta atagcggtgc agatgttcgt  1260
ggttatctgc attggagcct ggcagataat tatgaatggg caagcggttt tagcatgcgt  1320
tttggtctgc tgaaagttga ttataatacc aaacgtctgt attggcgtcc gagcgcactg  1380
gtttatcgtg aaattgcaac caatggtgca attaccgatg aaattgaaca tctgaatagc  1440
gttccgccgg ttaaaccgct gcgtcattaa                                    1470

SEQ ID NO: 17           moltype = DNA  length = 1470
FEATURE                 Location/Qualifiers
source                  1..1470
                        mol_type = other DNA
                        organism = synthetic construct
SEQUENCE: 17
atgtatagct ttccgaatag ctttcgcttt ggttggtccc aggcaggttt tcagagcgaa  60
atgggtaccc cgggtagcga agatccgaac accgattggt ataaatgggt gcatgatccg  120
gaaaatatgg cagcaggtct ggttagcggt gatctgccag aaaatggtcc gggttattgg  180
ggtaactata aaacatttca tgataacgca cagaaaatgg gtctgaaaat tgcacgtctg  240
```

-continued

```
aacgttgaat ggagtcgtat ttttccgaat ccgctgccgc gcccggagga ttttgatgaa  300
agcaaacagg atgttaccga agtggaaatt aacgaaaatg aactgaaacg tctggatgaa  360
tatgcaaata aagatgcact ggaccattat cgtgaaatct ttaaagatct gaaaagccgt  420
ggcctgtatt ttatcctgaa tatgtatcat tggccgctgc cgctgtggct gcatgatcct  480
attcgcgttc gtcgtggtga ttttaccggt ccgtctggtt ggctgagcac ccgtactgtt  540
tatgaatttg cacgttttag cgcttatatt gcttggaaat ttgatgatct ggttgatgaa  600
tatagcacta tgaatgaacc gaacgttgtt ggtggtctgg gttatgttgg tgttaaaagc  660
ggttttccgc ctggttatct gagctttgaa ctgtcccgcc gtgcaatgta taatattatt  720
caggcacatg cgcgtgccta tgatggtatt aaaagcgttt ctaaaaagcc ggttggcatt  780
atttatgcga atagcagctt tcagcctctg accgataaag atatggaagc agttgaaatg  840
gcagaaaatg ataatcgttg gtggtttttt gatgcgatca ttcgtggtga aattacccgt  900
ggtgatgaaa aaattgttcg tgatgatctg aaaggtcgtc tggattggat tggtgttaat  960
tattataccc gtaccgttgt taaacgtacc gaaaaaggtt atgttagcct gggtggttat  1020
ggtcatggtt gtgaacgtaa tagcgttagc ctggcaggtc tgccgaccag cgattttggt  1080
tgggaatttt ttccggaagg tctgtatgat gttctgacca aatattggaa tcgttatcat  1140
ctgtatatgt atgttaccga aaatggtatt gcagatgatg cagattatca gcgtccgtat  1200
tatctggtta gccatgttta tcaggttcat cgtgcaatta atagcggtgc agatgttcgt  1260
ggttatctgc attggagcct ggcagataat tatgaatggg caagcggttt tagcatgcgt  1320
tttggtctgc tgaaagttga ttataatacc aaacgtctgt attggcgtcc gagcgcactg  1380
gtttatcgtg aaattgcaac caatggtgca attaccgatg aaattgaaca tctgaatagc  1440
gttccgccgg ttaaaccgct gcgtcattaa                                  1470

SEQ ID NO: 18          moltype = AA  length = 489
FEATURE                Location/Qualifiers
source                 1..489
                       mol_type = protein
                       organism = synthetic construct
SEQUENCE: 18
MYSFPNSFRF GWSQAGFQSE MGTPGSEDPN TDWYKWVHDP ENMAAGLVSG DLPENGPGYW  60
GNYKTFHDNA QKMGLKIARL NVEWSRIFPN PLPRPQNFDE SKQDVTEVEI NENELKRLDE  120
YANKDALDHY REIFKDLKSR GLYFILNMYH WPLPLWLHDP IRVRRGDFTG PSGWLSTRTV  180
YEFARFSAYI AWKFDDLVDE YSTMNEPNVV GGLGYVGVKS GFPPGYLSFE LSRRAMYNII  240
QAHARAYDGI KSVSKKPVGI IYANSSFQPL TDKDMEAVEM AENDNRWWFF DAIIRGEITR  300
GDEKIVRDDL KGRLDWIGVN YYTRTVVKRT EKGYVSLGGY GHGCERNSVS LAGLPTSDFG  360
WEFFPEGLYD VLTKYWNRYH LYMYVTENGI ADDADYQRPY YLVSHVYQVH RAINSGADVR  420
GYLHWSLADN YEWASGFSMR FGLLKVDYNT KRLYWRPSAL VYREIATNGA ITDEIEHLNS  480
VPPVKPLRH                                                         489
```

What is claimed is:

1. A *Sulfolobus solfataricus*-β-glycosidase (SS-BGL) mutant for modifying ginsenoside, wherein the SS-BGL mutant is a mutant with the amino acid sequence of SEQ ID NO: 18;

wherein the SS-BGL mutant is formed by mutating asparagines at 128$^{th}$ position and 302$^{th}$ position of the amino acid sequence of SEQ ID NO: 1 of SS-BGL into aspartic acids respectively.

2. A gene encoding the SS-BGL mutant as claimed in claim 1.

3. A recombinant expression vector comprising the gene as claimed in claim 2.

4. The recombinant expression vector as claimed in claim 3, wherein the recombinant expression vector is formed by using a pET-24a(+) vector as an original expression vector.

5. A genetically engineered bacterium transformed by the recombinant expression vector as claimed in claim 3.

6. The genetically engineered bacterium as claimed in claim 5, wherein the genetically engineered bacterium is *Escherichia coli* BL21(DE3) host cell.

7. An SS-BGL mutant for modifying ginsenoside, wherein the amino acid sequence of the SS-BGL mutant is SEQ ID NO: 18.

* * * * *